United States Patent
Jayaraman

(10) Patent No.: US 11,179,545 B2
(45) Date of Patent: Nov. 23, 2021

(54) SYSTEM AND METHOD FOR DELIVERY OF THERAPEUTIC AGENT THROUGH A CATHETER

(71) Applicant: Swaminathan Jayaraman, Pleasanton, CA (US)

(72) Inventor: Swaminathan Jayaraman, Pleasanton, CA (US)

( * ) Notice: Subject to any disclaimer, the term of this patent is extended or adjusted under 35 U.S.C. 154(b) by 391 days.

(21) Appl. No.: 15/767,188

(22) PCT Filed: Oct. 12, 2016

(86) PCT No.: PCT/US2016/056559
§ 371 (c)(1),
(2) Date: Apr. 10, 2018

(87) PCT Pub. No.: WO2017/066262
PCT Pub. Date: Apr. 20, 2017

(65) Prior Publication Data
US 2019/0070389 A1    Mar. 7, 2019

Related U.S. Application Data
(60) Provisional application No. 62/240,029, filed on Oct. 12, 2015.

(51) Int. Cl.
*A61M 25/00* (2006.01)
*A61M 5/20* (2006.01)
(Continued)

(52) U.S. Cl.
CPC .......... *A61M 25/0084* (2013.01); *A61M 5/00* (2013.01); *A61M 5/158* (2013.01);
(Continued)

(58) Field of Classification Search
CPC .......... A61M 25/0084; A61M 25/0071; A61M 2025/0086; A61M 2025/0096; A61M 2025/0087; A61M 5/2053; A61M 5/158
See application file for complete search history.

(56) References Cited

U.S. PATENT DOCUMENTS 5,354,279 A * 10/1994 Hofling ............. A61M 25/0069
604/164.12
5,419,777 A     5/1995 Hofling
(Continued)

FOREIGN PATENT DOCUMENTS

RU      2129888      5/1999
WO      2017066262 A1    4/2017

OTHER PUBLICATIONS

International Search Report and Written Opinion dated Jan. 12, 2017 for PCT/US2016/56559.

*Primary Examiner* — Nathan R Price
*Assistant Examiner* — Anh Bui
(74) *Attorney, Agent, or Firm* — Fleit Intellectual Property Law; Paul D. Bianco; Gary S. Winer

(57) ABSTRACT

A system and method for delivering a therapeutic agent such as filler materials, biocompatible gels, and other substances through a catheter. The therapeutic agent can be a single component or multiple components that are delivered separately or mixed just prior to delivery or at the delivery site. The system and method use an automated delivery mechanism to maximize delivery of the therapeutic agent to the target tissue and minimize loss of the therapeutic agent within the catheter. The system and method are particularly useful for interventional approaches that deliver therapeutic agents to the wall of the heart.

20 Claims, 5 Drawing Sheets

(51) Int. Cl.
  *A61M 5/00* (2006.01)
  *A61M 5/158* (2006.01)
  *A61M 5/145* (2006.01)
  *A61M 5/315* (2006.01)
  *A61B 17/34* (2006.01)
  *A61B 17/00* (2006.01)

(52) U.S. Cl.
  CPC ....... *A61M 5/2053* (2013.01); *A61B 17/3478* (2013.01); *A61B 2017/00247* (2013.01); *A61M 5/14526* (2013.01); *A61M 5/31581* (2013.01); *A61M 25/0026* (2013.01); *A61M 2025/0086* (2013.01); *A61M 2025/0087* (2013.01); *A61M 2210/125* (2013.01)

(56) References Cited

U.S. PATENT DOCUMENTS

| | | | |
|---|---|---|---|
| 6,360,749 B1 | 3/2002 | Jayaraman | |
| 6,659,982 B2 | 12/2003 | Douglas et al. | |
| 6,685,627 B2 | 2/2004 | Jayaraman | |
| 7,390,293 B2 | 6/2008 | Jayaraman | |
| 8,715,156 B2 | 5/2014 | Jayaraman | |
| 9,011,380 B2 | 4/2015 | Tkebuchava | |
| 2002/0177772 A1* | 11/2002 | Altman | A61B 18/1492 600/431 |
| 2005/0177109 A1* | 8/2005 | Azzolini | B01F 13/0023 604/151 |
| 2014/0088502 A1* | 3/2014 | Matheny | A61K 35/32 604/121 |
| 2015/0005740 A1* | 1/2015 | Foster | A61M 25/0084 604/506 |

\* cited by examiner

SYSTEM AND METHOD FOR DELIVERY OF THERAPEUTIC AGENT THROUGH A CATHETER

FIELD OF THE DISCLOSURE

The disclosure relates to a system and method for delivering a therapeutic agent such as a filler material, biocompatible gels, and other substances through a catheter.

BACKGROUND

There is a significant challenge in delivery of therapeutic agents through long catheters using interventional approaches. As the access vessels are typically in the femoral artery (leg) the catheter has to wind all the way up into the heart and then go through the mitral valve and then reach the wall of the ventricle. The catheter has to be in contact very close to the ventricular wall for the agent(s) to be delivered properly.

In the case of congestive heart failure, one treatment that has effectiveness is the introduction of materials to modify the geometry and/or properties of heart tissue. This treatment is described in U.S. Pat. Nos. 8,715,156; 7,390,293; 6,685,627; and 6,360,749, each of which is incorporated by reference in its entirety herein. Most of the material fillers and other biocompatible materials that are delivered within the walls of the ventricle need to be delivered fast as they are one part, two part, or three part systems which gel within a short period of time. Delivering these systems by a syringe using manual techniques is probably not the most optimum approach as there are significant losses within the catheter and very little material actually gets delivered into the wall of the heart.

Despite these limitations, medical professionals still utilize these systems as they provide numerous advantages relative to alternative approaches. As a result, what is needed is a system and method for delivering therapeutic agent(s) such as a filler material, biocompatible gels, and other substances through a catheter.

SUMMARY OF THE DISCLOSURE

A system for delivery of a therapeutic agent through a catheter to target tissue includes an injection catheter having a head at a distal end, a proximal end opposite the distal end, and a shaft extending between the distal and proximal ends. A plurality of needles is disposed in the catheter head movably between a retracted position in which the needles are located within the catheter head and an extended position in which front ends of the needles project from the catheter head through openings formed therein. Each of the plurality of needles is hollow so as to have a needle passage. The system also includes a multi-lumen hose upon which the needles are mounted, with the multi-lumen hose longitudinally movably supported within the catheter and having a plurality of individual passages. Each of the plurality of individual passages is in fluid communication with a respective one of the needle passages. An activation mechanism is on the catheter shaft for longitudinally moving the multi-lumen hose to selectively deploy the needles into the extended position and retracted position. The activation mechanism is operatively associated with the catheter shaft and the multi-lumen hose. An automated delivery device has a controller for controlling rate of delivery and timing of release of the therapeutic agent and at least one chamber containing the therapeutic agent. Each of the at least one chamber has an outlet in fluid communication with one of the individual passages for transmitting the therapeutic agent to the needles for injection into the target tissue.

In an embodiment, the at least one chamber includes a first chamber having a first syringe body and a first plunger; and a second chamber having a second syringe body and a second plunger. The controller is coupled to the first and second plungers for controlling rate of delivery and timing of release of the therapeutic agent.

The first syringe body can contain a first component of the therapeutic agent and the second syringe body can contain a second component of the therapeutic agent. Alternatively, the first syringe body can contain a first therapeutic agent and the second syringe body can contain a second therapeutic agent.

In an embodiment, the first and second plungers are coupled to a pusher for moving the first and second plungers. A motor is coupled to the pusher, with the motor controlled by the controller for effecting movement of the pusher. In an exemplary embodiment, a drive screw couples the motor to the pusher.

In another embodiment, the pusher has a first portion coupled to the first plunger and a second portion coupled to the second plunger, with the first portion separately movable from the second portion. The first portion of the plunger is coupled to a first motor and the second portion of the plunger is coupled to a second motor.

Another aspect of the disclosure relates to a method for delivery of a therapeutic agent through a catheter to target tissue. The method comprises the steps of: positioning an injection catheter adjacent the target tissue; deploying a plurality of needles from a distal end of the injection catheter into the target tissue; and activating an automated delivery system coupled to the injection catheter. The automated delivery system has at least one chamber containing the therapeutic agent and a controller for controlling rate of delivery and timing of release of the therapeutic agent. Activation of the automated delivery system enables flow of the therapeutic agent from the at least one chamber through the injection catheter and plurality of needles and into the target tissue.

Although the method can be used for different tissues, in one embodiment the target tissue is myocardium. A contrast agent can be added to the therapeutic agent. This addition can occur during delivery of the therapeutic agent into the myocardium or before delivery of the therapeutic agent into the myocardium. The contrast agent can be used for visualizing delivery of the therapeutic agent. The contrast agent can also be used to visualize accumulation of the therapeutic agent in the myocardium. Further, the contrast agent can be used to determine motion of a wall of the heart.

In situations in which the therapeutic agent includes a first component and a second component, the first component of the therapeutic agent is delivered through a first one of the plurality of needles and the second component of the therapeutic agent is delivered through a second one of the plurality of needles.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION

Figure 1:
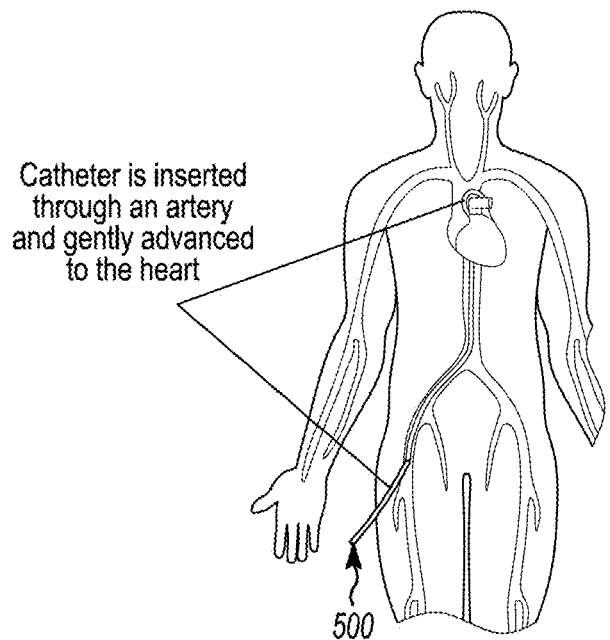
FIG. 1 schematically shows a catheter inserted through the femoral artery and advanced to the heart.

As required, embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

The term "therapeutic agent" as used herein is defined as a material or substance with a beneficial and desirable effect. Therapeutic agents include a range of compounds and substances, both natural and man-made, and combinations thereof. The therapeutic agents can include pharmaceutically active agents, pharmaceutically active materials, drugs, and biologically active agents. Other non-limiting examples of the types of therapeutic agents are set forth in the patents identified above in the Background section.

In this regard, the therapeutic agents can be:

A. Mixed with contrast agents during delivery of the material into the intended site (e.g. myocardium).

B. Mixed with contrast agents just before delivery of the material (e.g. hydrogels, alginates etc.)

C. Interspersed with contrast agents during or after delivery.

The contrast agents are used to visualize the delivery of the filling material during and after implantation and also for follow up to see the wall motion and also to determine where the filling materials are accumulated in the tissue. The contrast agents may be non-ionic or ionic agents. CT contrast agents and MRI contrast agents may also be used along with the filling material. If a two part therapeutic agent (which helps in the gelling process) when injected is used, then the contrast agent may be mixed with one of the materials before and then mixed with the second agent for delivery.

Two aspects of the disclosure involve:

1. The positioning of a catheter which has multiple needles at the distal ends (relative to the surgeon) to go into the wall of the ventricle and deliver the substance.
2. A quick and easy delivery approach of injecting the materials through such a catheter and to deliver the substance with minimal or without any loss of the materials in the catheter.

The system and method according to the disclosure include:

1. A standard conventional deflectable catheter is introduced into the heart and is positioned near the wall of the ventricle where the substance needs to be introduced.
2. The injection catheter is now introduced into the deflectable catheter so that the injection catheter is guided to the position where the material needs to be delivered.
3. Once the injection catheter is in place, the needles are introduced into the ventricle and at the end of the catheter an automated delivery mechanism is attached.
4. The automated delivery system has a small cavity where the material to be injected can be housed.
5. Connected to the housing is a motor attached which gets activated by the surgeon.
6. Once the motor is activated a plunger located in front moves and this pushes inward towards the housing which accommodates the substance to be injected.
7. The speed of the motor assembly can be adjusted to deliver the substance quickly without any back bleeding or the material coagulating within the catheter.

FIG. 1 schematically shows a sheath or deflectable catheter 500 inserted through the femoral artery and advanced to the heart. For left heart catheterization and coronary angiography, the femoral artery in the leg has been the traditional access site. However, the radial artery in the wrist can also be used. As is well-known, the artery is accessed with a needle, allowing insertion of a thin guide wire and placement of the sheath. Through the sheath, catheters are advanced into the heart with the use of x-ray guidance or other monitoring techniques.

Using the x-ray guidance or other monitoring techniques, the injection catheter is now introduced into the deflectable catheter so that it is guided to the position where the material needs to be delivered. The disclosure also contemplates that the injection catheter can be used without a deflectable catheter or sheath.

Figure 2:
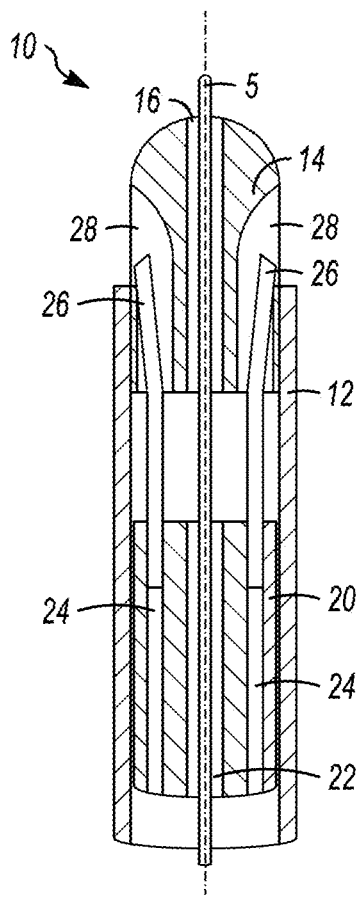
FIG. 2 shows a distal end of an injection catheter with a mechanism to effect retraction and extension of injection needles with the injection needles retracted.
Figure 3:
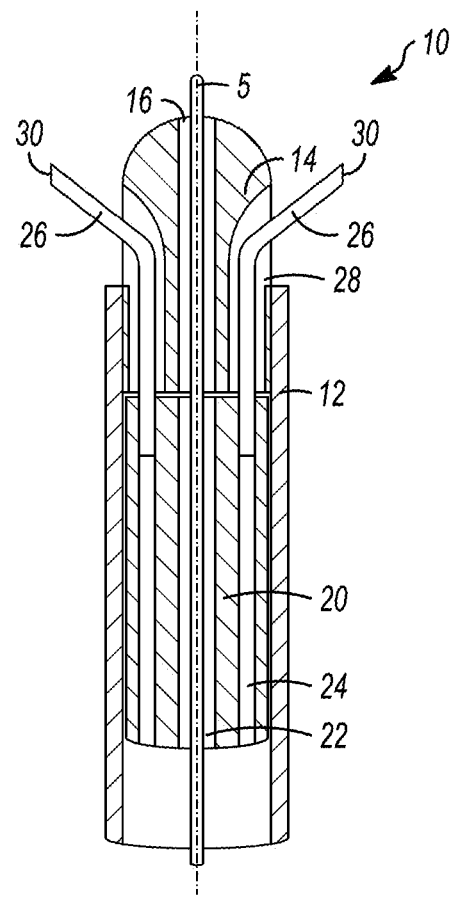
FIG. 3 shows the distal end of the injection catheter of FIG. 2 with the injection needles extended.

FIGS. 2 and 3 show one embodiment of the distal end of an injection catheter 10 which may be inserted into a body on a guide wire in a well-known manner. The catheter includes an outer shank 12 at whose end a catheter head 14 is mounted. The catheter head 14 can be firmly connected to the outer shank 12 by welding or cementing. The catheter head 14 includes a longitudinally extending passage 16 for receiving a guide wire 5. Alternatively, the passageway for a guide wire can be located on the outer surface of the injection catheter. Further, an inner hose 20 is disposed within the outer shank 12 so as to be longitudinally movable therein. The hose has a central passage 22 in which the guide wire 5 is disposed. The hose is further provided with passages 24 (lumen) with hollow needles 26 mounted thereon at the front end of the catheter. The catheter head 14 includes longitudinal grooves or recesses of a suitable shape which terminate in openings 28 at the side of the catheter head or in the rounded or conical front end of the catheter head.

The hollow needles 26 are pre-bent (or made of a memory metal) so that, in the passage 24, they are maintained under a mechanical stress which presses them outwardly onto the outer shank 12. They are prevented from pivoting by side engagement with the groove walls of the opening 28. By sliding the inner hose 20 forwardly within the outer shank 12 the needles are moved forward and, as a result of their stress condition, extend outwardly for engagement with the adjacent vessel wall or they may even pierce the vessel wall depending on how the operator, based on his experience, operates the device. It is also possible to forcefully bend the needles outwardly by moving them along the inner wall of the openings 28. After the needles 26 are extended a therapeutic agent or multiple therapeutic agents can be supplied to the tissue through each of the passages 24 and the needle channel which is shown in other drawings. The therapeutic agent(s) is/are emitted from the end faces 30 of the needles 26.

As each needle is associated with its own passage or lumen, a different therapeutic agent could be emitted from each needle. This is particularly useful when the therapeutic agent is a settable material, such as a gel, made of two or more components. Further, although two needles are shown, the disclosure contemplates any suitable number of needles can be used. The end faces 30 of the needles are preferably so arranged that, in longitudinal direction, they extend parallel to the catheter axis. This means that the area 30 abuts the vessel wall flatly and can be inserted into the tissue only by application of an increased force.

It is of course possible to use other needle front face cuts, depending on a particular application, to achieve greater tissue penetration and/or penetration in a different pattern. In the embodiment according to FIGS. 2 and 3 several needles 26 are provided and arranged such that they project from the catheter 10 concurrently at several sides of the catheter 10 by forward sliding of the inner hose 20 such that the catheter is supported on the vessel wall from all sides and is centrically supported. Then the surfaces 30 clearly engage the wall or the needles pierce the wall of the tissue if they are cut for that purpose and the unintended washing away of the therapeutic agent is prevented. Also, good contact of the end face 30 with the vessel wall is achieved. The disclosure also contemplates that the needles can be advanced separately.

Figure 4:
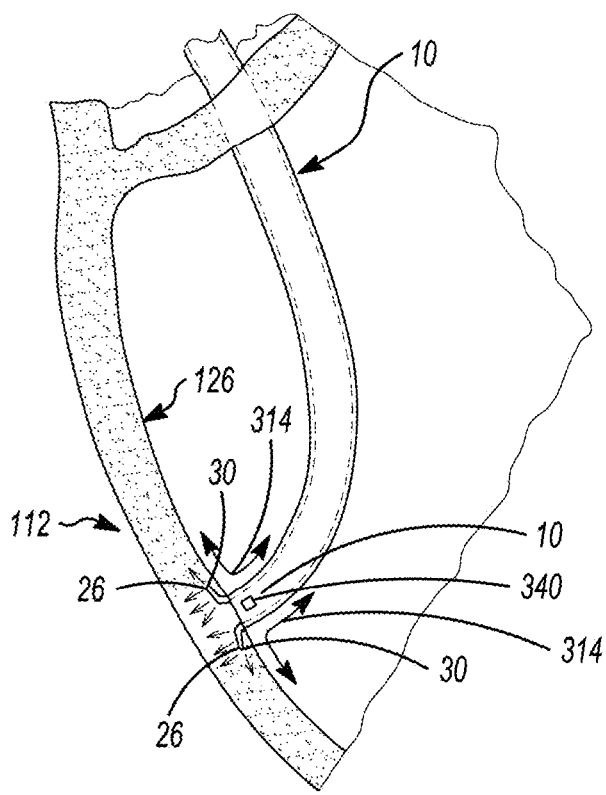
FIG. 4 is a partial cross section of the right ventricle of the heart showing an exemplary insertion of the injection needles of the catheter of the disclosure penetrating the heart wall.

Referring now to FIG. 4, the distal end of the catheter 10 is shown engaging an exemplary site within the right ventricle of the heart 112. In this example, the extensible needles 26 have been deployed (arrows 314) into the myocardium 126. Once extended, each needle can deliver a therapeutic and/or diagnostic agent via a tip opening 30 and one or more openings along (at least) the medial edge of the needle's exposed shaft.

Note that the addition of a special radio-opaque marker 340 (for example) on the distal tip of the catheter 10, as desired, allows one to determine the position of the catheter tip easily on an X-ray screen. Moreover, this ability facilitates the definition of the rotation and angle of the position of the distal end of the catheter of the present disclosure. This design also allows the determination of whether the needles 26 are extended or retracted.

Figure 5:
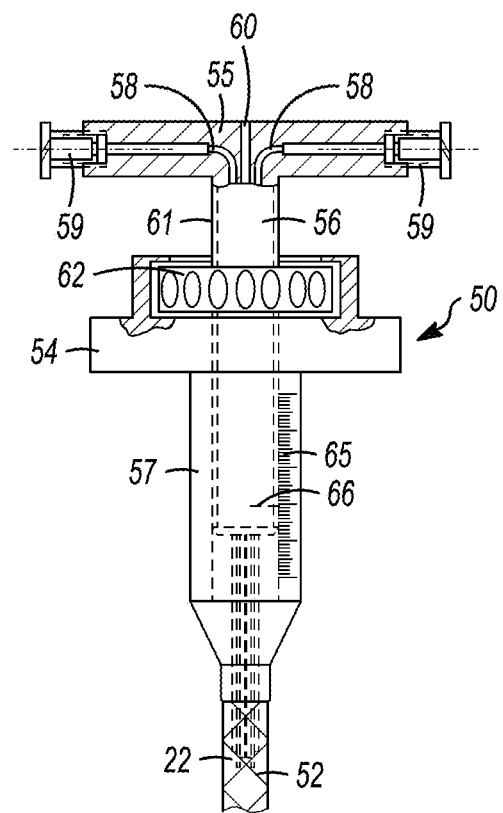
FIG. 5 shows an embodiment of an activation mechanism for effecting extension and retraction of the injection needles.

Referring now to FIG. 5, an exemplary embodiment of an activation mechanism for effecting extension of the injection needles is shown. This activation mechanism, generally designated with numeral 50, comprises essentially two parts 54 and 55 referred to herein as the stationary part 54 and as the movable part 55, respectively. The movable part 55 includes a thrust plunger 56 which is slidable in a cylinder 57 of the stationary part 54 and has connected thereto the proximal end of the injection catheter 10, the movable part 55 includes therapeutic agent inlets 59 and channels 58 providing fluid flow communication between the therapeutic agent inlets 59 and the corresponding injection needles. The movable part 55 further includes a bore 60 which extends into the guide volume within the catheter stem. The thrust plunger 56 has a thread threadedly engaged with a knurled nut 62 which is captively supported on the stationary part 54 and rotatable to displace the thrust plunger 56 inwardly of the cylinder 57 and thereby effect a corresponding movement of the injection needles connected thereto. The cylinder 57 may be provided with a scale 65 and the thrust plunger 56 with an indicating line 66 for indicating the extent of plunger displacement and thereby allowing it to be accurately controlled. The cylinder 57 has connected thereto the catheter stem 22 which may have a stainless-steel wire mesh 52 incorporated therein in order to stabilize it against undesirable longitudinal elongation and compression while the injection needles are being displaced.

Figure 6:
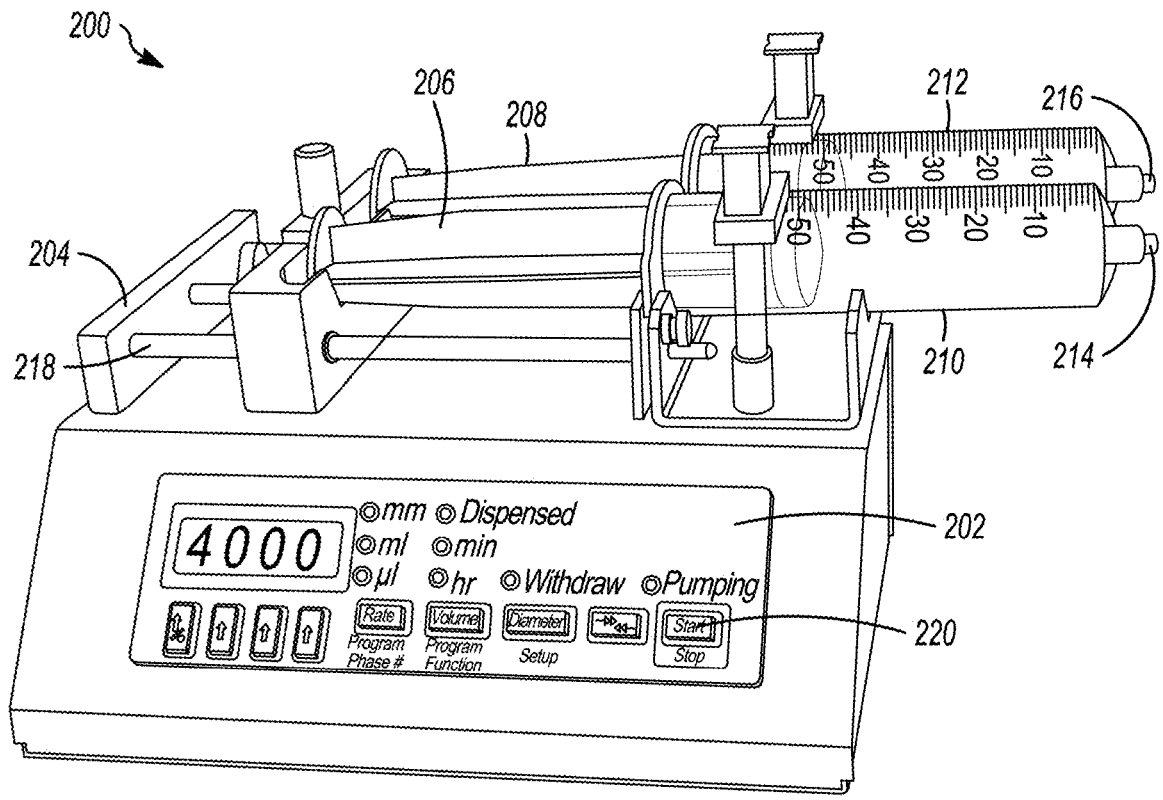
FIG. 6 shows an embodiment of the automated delivery system for delivery of the therapeutic agent(s).

FIG. 6 shows an exemplary embodiment of an automated delivery system 200 according to the disclosure. System 200 is used to control the rate of delivery and timing of the therapeutic agents. In particular, system 200 includes a controller 202 for controlling the timing and rate of movement of pusher 204, which is coupled to plungers 206 and 208 of syringes 210 and 212, respectively. Syringes 210 and 212 contain the therapeutic agent. In one embodiment, syringe 210 contains a first component of the therapeutic agent and syringe 212 contains a second component of the therapeutic agent. In another embodiment, syringe 210 contains a first therapeutic agent and syringe 212 contains a second therapeutic agent, with the therapeutic agent having a combined effect.

As plungers 206 and 208 move via pusher 204, the therapeutic agent is expelled out of syringes 210 and 210 through ends 214 and 216. As ends 214 and 216 are coupled to inlets 59 (FIG. 4), the components of therapeutic agent are delivered through channels 24 of injection catheter 10. In one embodiment, pusher 204 is made of two separately movable parts so that the rate, timing, and/or volume of each component of the therapeutic agent can be separately controlled. In another embodiment, pusher 204 is a unitary structure or otherwise moves both plungers 206 and 208 together to that the rate, timing, and/or volume of each component of the therapeutic agent are the same. Although system 200 is shown with two syringes, the disclosure contemplates other embodiments with more or less syringes, depending on the therapeutic agent(s) to be delivered.

Figure 10:
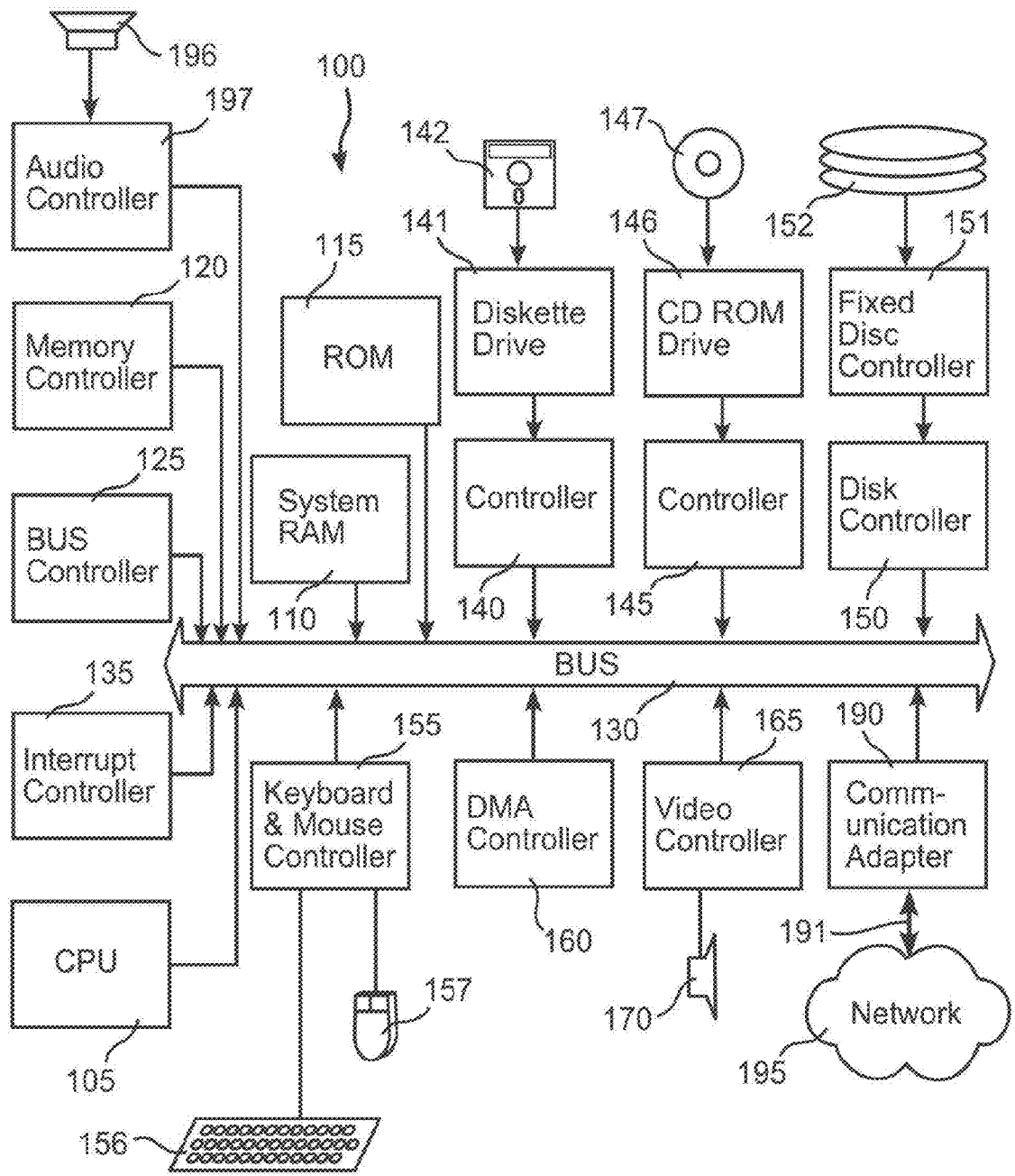
FIG. 10 is schematic illustration of one exemplary computer system for controlling the delivery system of FIGS. 6-8.

Pusher 204 is moved by one (if plungers 206 and 208 move together) or two (if plungers 206 and 208 move separately) motors which cause drive screw 218 to rotate thereby moving pusher 204. The disclosure contemplates that other suitable syringe pump configurations can be used. System 200 is controlled by keypad 220, used to program a microprocessor of system 200. Alternatively, system 200 can be controlled by a separate computer system 100 as shown in FIG. 10.

Figure 7:
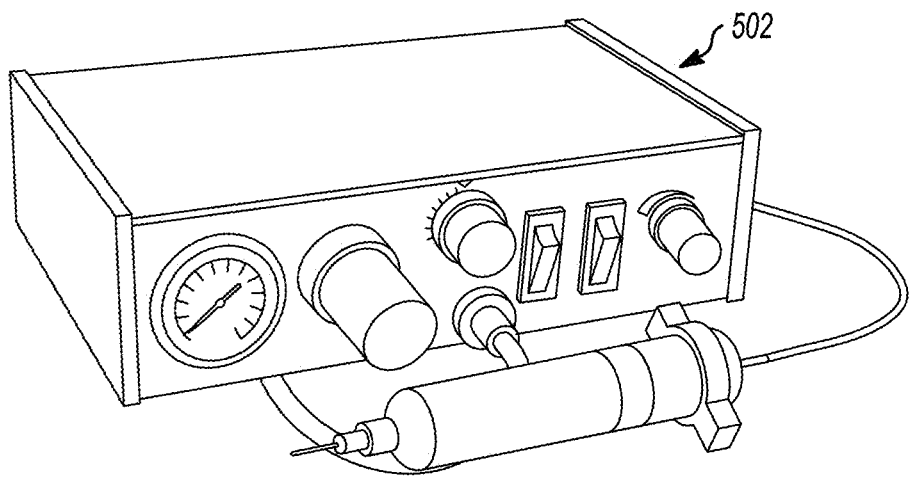
FIG. 7 shows another embodiment of the automated delivery system for delivery of the therapeutic agent(s).
Figure 8:
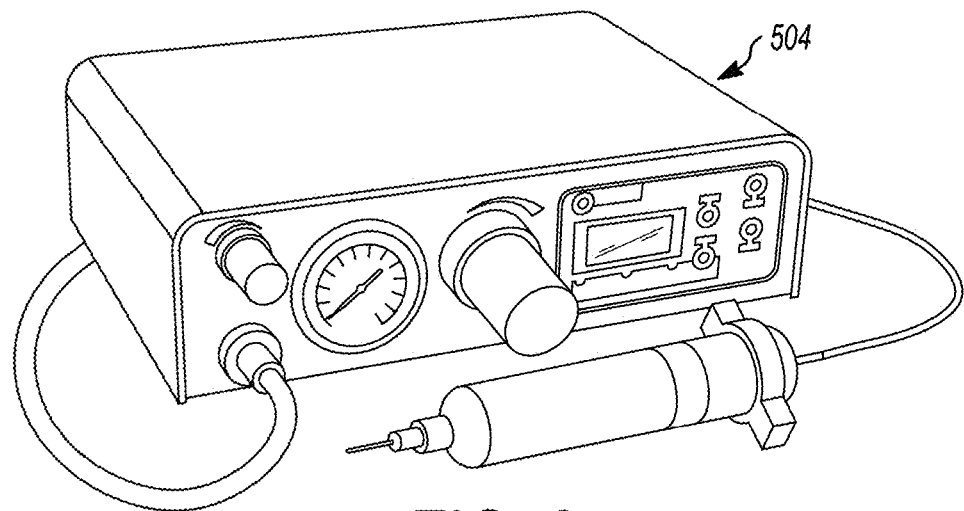
FIG. 8 shows another embodiment of the automated delivery system for delivery of the therapeutic agent(s).
Figure 9A:
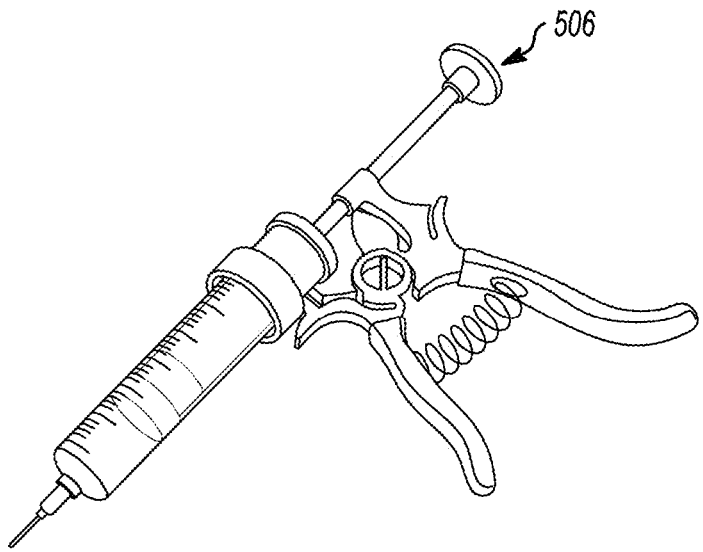
FIGS. 9A and 9B show two embodiments of a manual delivery system for delivery of the therapeutic agent(s).
Figure 9B:
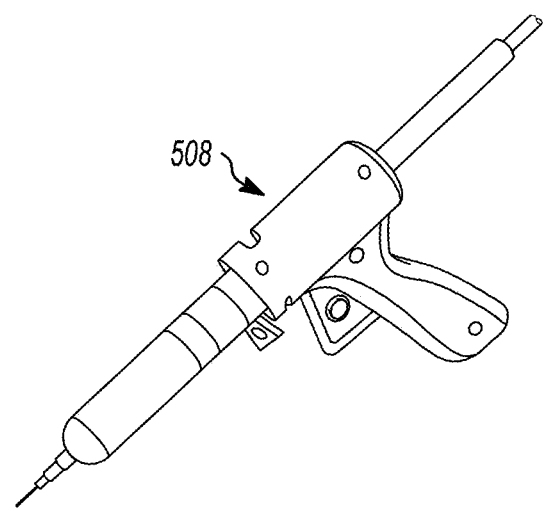

FIGS. 7 and 8 show commercially available (Fisnar, Pine Brook, N.J.) dispensing and delivery mechanisms which can be used along with the injection catheter according to the disclosure for delivery of the therapeutic agent(s). FIGS. 9A and 9B show commercially available (Fisnar, Pine Brook, N.J.) manually operated dispensing and delivery mechanisms which can be used along with the injection catheter according to the disclosure for delivery of the therapeutic agent(s). As these figures show, the mechanism can be a digital pneumatic delivery system 502, a digital dispenser 504, or a volumetric hand dispenser 506, 508 which can be used to attach to the syringe which contains the therapeutic agent(s) to the injection catheter.

Computer system 100 includes at least one central processing unit (CPU) 105, or server, which may be implemented with a conventional microprocessor, a random access memory (RAM) 110 for temporary storage of information, and a read only memory (ROM) 115 for permanent storage of information. A memory controller 120 is provided for controlling RAM 110.

A bus 130 interconnects the components of computer system 100. A bus controller 125 is provided for controlling bus 130. An interrupt controller 135 is used for receiving and processing various interrupt signals from the system components.

Mass storage may be provided by diskette 142, CD or DVD ROM 147, flash or rotating hard disk drive 152. Data and software, including software 400 of the disclosure, may be exchanged with computer system 100 via removable media such as diskette 142 and CD ROM 147. Diskette 142 is insertable into diskette drive 141 which is, in turn, connected to bus 130 by a controller 140. Similarly, CD ROM 147 is insertable into CD ROM drive 146 which is, in turn, connected to bus 130 by controller 145. Hard disk 152 is part of a fixed disk drive 151 which is connected to bus 130 by controller 150. It should be understood that other storage, peripheral, and computer processing means may be developed in the future, which may advantageously be used with the disclosure.

User input to computer system 100 may be provided by a number of devices. For example, a keyboard 156 and mouse 157 are connected to bus 130 by controller 155. An audio transducer 196, which may act as both a microphone and a speaker, is connected to bus 130 by audio controller 197, as illustrated. It will be obvious to those reasonably skilled in the art that other input devices, such as a pen and/or tablet, Personal Digital Assistant (PDA), mobile/cellular phone and other devices, may be connected to bus 130 and an appropriate controller and software, as required. DMA controller 160 is provided for performing direct memory access to RAM 110. A visual display is generated by video controller 165 which controls video display 170. Computer system 100 also includes a communications adapter 190 which allows the system to be interconnected to a local area network (LAN) or a wide area network (WAN), schematically illustrated by bus 191 and network 195.

Operation of computer system 100 is generally controlled and coordinated by operating system software, such as a Windows system, commercially available from Microsoft Corp., Redmond, Wash. The operating system controls allocation of system resources and performs tasks such as processing scheduling, memory management, networking, and I/O services, among other things. In particular, an operating system resident in system memory and running on CPU 105 coordinates the operation of the other elements of computer system 100. The present disclosure may be implemented with any number of commercially available operating systems.

One or more applications, such as an HTML page server, or a commercially available communication application, may execute under the control of the operating system, operable to convey information to a user.

All references cited herein are expressly incorporated by reference in their entirety. It will be appreciated by persons skilled in the art that the present disclosure is not limited to what has been particularly shown and described herein above. For example, the disclosure focuses on delivery of therapeutic agents to heart tissue, but the disclosure contemplates any application in which one or more therapeutic agents are delivered via a catheter.

In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. A system for delivery of a therapeutic agent through a catheter to a target tissue, the system comprising:
    a catheter having a head at a distal end, a proximal end opposite the distal end, and a shaft extending between the distal and proximal ends;
    a plurality of needles disposed in the head movably between a retracted position in which the needles are located within the head and an extended position in which front ends of the needles project from the head through openings formed therein, each needle of the plurality of needles being hollow so as to have a needle passage;
    a multi-lumen hose upon which the plurality of needles is mounted, the multi-lumen hose longitudinally movably supported within the catheter and having a plurality of individual passages, each individual passage of the plurality of individual passages in fluid communication with a respective one of the needle passages;
    an activation mechanism arranged on the shaft of the catheter and configured for longitudinally moving the multi-lumen hose to selectively deploy the plurality of needles into the extended position and retracted position, the activation mechanism including:
        a movable part including a threaded thrust plunger, the threaded thrust plunger affixed to the multi-lumen hose at the proximal end of the catheter,
        a stationary part affixed to the shaft of the catheter and including a cylinder sized to slidingly receive the threaded thrust plunger, and
        a rotatable threaded nut captured by the stationary part and threadably engaged with the threaded thrust plunger to cause the threaded thrust plunger to slide within the cylinder when the rotatable threaded nut is rotated to thereby move the multi-lumen hose and mounted plurality of needles distally and proximally within the catheter shaft; and
    an automated delivery device coupled with the catheter having a controller and at least one chamber and configured for automatic operation of the system, the controller configured for controlling rate of delivery and timing of release of the therapeutic agent and the at least one chamber in fluid communication with the individual passages of the multi-lumen hose and configured for containing the therapeutic agent.

2. The system of claim 1, wherein the at least one chamber includes a first chamber having a first syringe body and a first plunger coupled to the controller and a second chamber having a second syringe body and a second plunger coupled to the controller.

3. The system of claim 2, wherein the first syringe body contains a first therapeutic agent, or a first component of the therapeutic agent and the second syringe body contains a second therapeutic agent, or a second component of the therapeutic agent.

4. The system of claim 2, wherein the first and second plungers are coupled to a pusher configured for moving the first and second plungers.

5. The system of claim 4, further comprising a motor coupled to the pusher, the motor controlled by the controller and arranged for effecting movement of the pusher.

6. The system of claim 5, wherein the motor is coupled to the pusher with a drive screw.

7. The system of claim 4, wherein the pusher has a first portion coupled to the first plunger and a second portion, separately movable from the first portion, coupled to the second plunger.

8. The system of claim 7, wherein the first portion of the pusher is coupled to a first motor and the second portion of the pusher is coupled to a second motor.

9. A method for delivery of a therapeutic agent through a catheter to a target tissue, the method comprising:
positioning the catheter according to claim 1 adjacent the target tissue;
deploying the plurality of needles from a distal end of the catheter into the target tissue; and
activating the automated delivery system coupled to the catheter thereby enabling flow of the therapeutic agent from the at least one chamber through the catheter and through the plurality of needles into the target tissue.

10. The method of claim 9, wherein the target tissue is myocardium.

11. The method of claim 10, further comprising adding a contrast agent to the therapeutic agent.

12. The method of claim 11, comprising adding the contrast agent to the therapeutic agent before or during delivery of the therapeutic agent into the myocardium.

13. The method of claim 12, further comprising visualizing delivery of the therapeutic agent.

14. The method of claim 13, further comprising using the contrast agent to determine motion of a wall of a heart.

15. The method of claim 9, wherein the therapeutic agent includes a first component and a second component.

16. The method of claim 15, further comprising delivering the first component of the therapeutic agent through a first needle of the plurality of needles and delivering the second component of the therapeutic agent through a second needle of the plurality of needles.

17. The system of claim 1, further comprising a radio-opaque marker disposed at the distal end of the catheter, the radio-opaque marker configured for determining the position, rotation, and angle of the distal end of the catheter, for determining whether the plurality of needles are in an extended or retracted position, and for visualizing delivery of the therapeutic agent to the target tissue.

18. A system for forming a therapeutic agent at a target tissue by delivering components of the therapeutic agent through a catheter to the target tissue, the system comprising:
a catheter having a head at a distal end, a proximal end opposite the distal end, and a shaft extending between the distal and proximal ends;
a plurality of needles disposed in the catheter and movable between a retracted position in which the needles are disposed in the head of the catheter and an extended position in which front ends of the needles project from the head of the catheter through openings formed therein, each needle of the plurality of needles having a needle passage;
a hose upon which the plurality of needles is mounted, the hose longitudinally movably supported within the catheter and having a plurality of individual hose passages, each hose passage of the plurality of individual hose passages in fluid communication with a respective one of the needle passages;
an activation mechanism arranged on the shaft and configured for longitudinally moving the hose to thereby move the plurality of needles between the extended and retracted positions; and
an automated delivery device configured for automatic operation of the system, the automated delivery device including;
a first syringe body having a first plunger, the first syringe body configured for delivering a first component of the therapeutic agent to the target tissue;
a second syringe body having a second plunger, the second syringe body configured for delivering a second component of the therapeutic agent to the target tissue;
a controller coupled to the first and second plungers and configured for controlling rate of delivery and timing of release of the first and second components of the therapeutic agent;
a pusher having a movable first portion and a second portion separately movable from the first portion, the first portion coupled to the first plunger and the second portion coupled to the second plunger;
a first motor coupled to the first portion of the pusher and configured for moving the first plunger; and
a second motor coupled to the second portion of the pusher and configured for moving the second plunger;
wherein when the first plunger is moved by action of the first motor on the first portion of the pusher the first component of the therapeutic agent is expelled from the first syringe body into the activation mechanism through an inlet formed therein, passed through a hose passage to a needle passage, and expelled from the needle passage at the target tissue; and
wherein when the second plunger is moved by action of the second motor on the second portion of the pusher, the second component of the therapeutic agent is expelled from the second syringe body into the activation mechanism through an inlet formed therein, passed through a hose passage to a needle passage, and expelled from the needle passage at the target tissue, thereby combining with the first component to form the therapeutic agent at the target tissue.

19. The system of claim 18, wherein the target tissue is myocardium.

20. The system of claim 19, wherein the first component and the second component are components of a biocompatible gel configured to solidify after delivery to the myocardium, thereby forming the therapeutic agent.

* * * * *